United States Patent [19]

Veale

[11] Patent Number: 5,005,563

[45] Date of Patent: Apr. 9, 1991

[54] MOBILE-CERVICAL EXTENSION AND SUPPORTING APPARATUS

[76] Inventor: Charles J. Veale, 1456 Opelika Rd., Auburn, Ala. 36830

[21] Appl. No.: 539,541

[22] Filed: Jun. 18, 1990

[51] Int. Cl.$^5$ .............................................. A61F 5/01
[52] U.S. Cl. .................................. 128/75; 128/87 B; 128/DIG. 23; 128/76 R
[58] Field of Search ............... 128/69, 75, 76 R, 87 B, 128/846, DIG. 23

[56] References Cited

U.S. PATENT DOCUMENTS

| | | | |
|---|---|---|---|
| 2,807,260 | 9/1957 | TeuPel | 128/DIG. 23 X |
| 2,820,455 | 1/1958 | Hall | 128/DIG. 23 X |
| 3,776,224 | 12/1973 | McFarland | 128/75 |

Primary Examiner—Richard J. Apley
Assistant Examiner—L. Thomas
Attorney, Agent, or Firm—Jennings, Carter, Thompson & Veal

[57] ABSTRACT

A mobile cervical brace for support, immobilization, and extension of the cervical vertebrae utilizing a base portion, a cranial support member selectively movable by an extension component relative to the base of the brace. Movement of the cranial support member is accomplished by a worm screw which engages and disengages threaded slots of a depending guide of the extensions means affixed to cranial support member to move the cranial support member relative to the base of my brace.

13 Claims, 4 Drawing Sheets

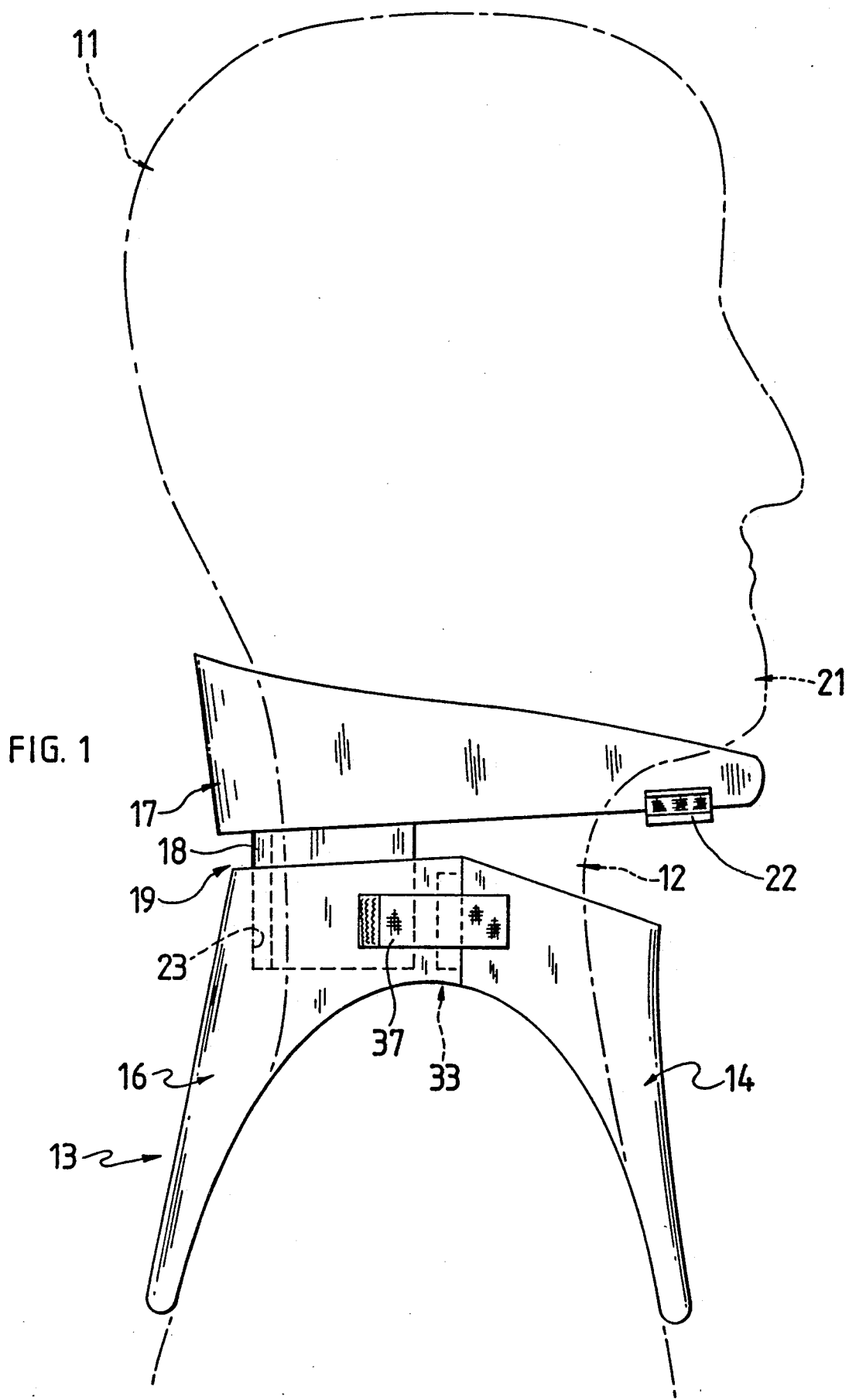

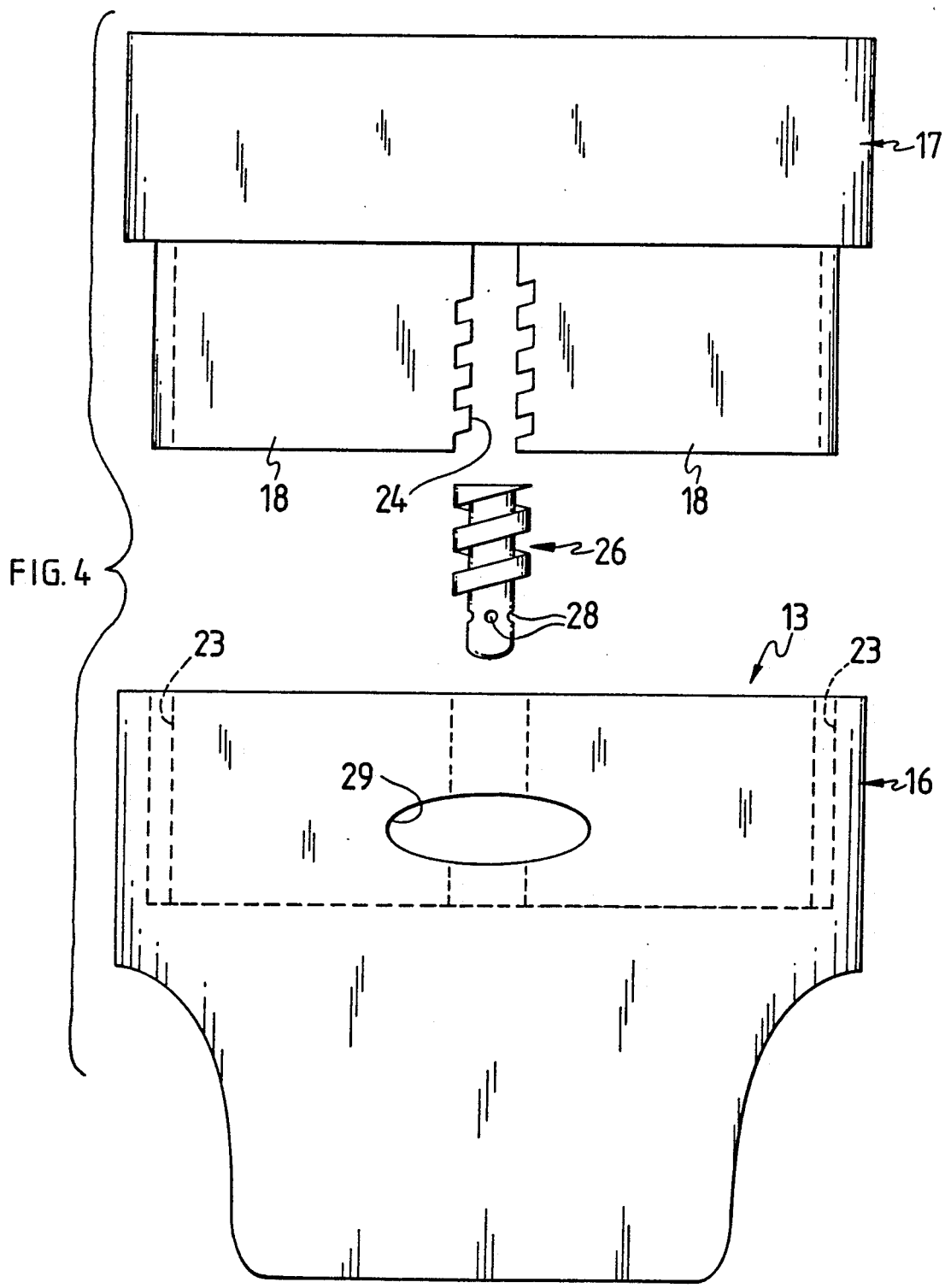

MOBILE-CERVICAL EXTENSION AND SUPPORTING APPARATUS

FIELD OF INVENTION

The present invention relates to the field of medicine, and more particularly to the treatment of the cervical vertebrae. In even greater particularity, the invention relates to the selective extension of the cervical vertebrae using a brace.

BACKGROUND OF THE INVENTION

The use of portable neck braces to immobilize the head, neck and sternum in proper alignment subsequent to an injury, as a result of trauma or disease has been widely used in the medical field for some time, especially in the field of medical emergency medicine. Numerous United States patents as well as foreign patents have disclosed a portable neck brace—U.S. Pat. Nos. 4,854,306; 4,886,052; 4,628,913; PCT/US82/01403; 4,708,129. The above patents disclose various apparatus which align and immobilize the neck and/or cervical vertebrae. Further, the devices disclosed in the above patents allow the user to remain mobile. Specifically, the above patents disclose a design of a "U" shape which fits around the user's neck. Some of the designs disclose the use of a sternum and clavicle member for greater stability. However, none of the above disclose an apparatus which is both portable and capable of applying variable upward pressure to the skull, thereby, simultaneously resulting in immobilization, stabilization, and extension of the cervical vertebrae as is provided by the present invention. The present invention provides a cranial support means which is movable relative to the base thus allowing the cranial support means to be extended to various positions causing tension to be placed upon the cervical vertebrae without losing mobility.

SUMMARY OF THE INVENTION

It is the object of this invention to provide an apparatus for support, stabilization and extension of the cervical vertebrae subsequent to an injury as a result of trauma or disease.

A further object of the invention is to provide an apparatus which while supporting and stabilizing the cervical vertebrae is capable of applying upward force to the skull resulting in extension and proper alignment of the cervical vertebrae.

Yet another object of the invention is to allow the user to be mobile while an extending force is being applied to the cervical vertebrae.

It should be noted that prior to the development of this invention portable cervical braces/neck braces merely resulted in stabilization and immobilization of the head and neck area. The present invention accomplishes the above objects and applies tension on the cervical vertebrae without the utilization of a non-mobile apparatus. Further, such extension and application of tension is accomplished without discomfort to the user as result of positioning on the user's skull either by screws, a halo or other type of extension apparatus known in the medical field.

BRIEF DESCRIPTION OF THE DRAWINGS

Apparatus embodying features of my invention are depicted schematically in the accompanying drawings which form a portion of this disclosure, wherein:

FIG. 1 is a right elevational view of my brace illustrating the use of the brace by a human user showing the posterior base member and the anterior base member forming one base unit which is engaged to the cranial support means by the extension means;

FIG. 4 is a posterior view of the cranial support means and the posterior base member illustrating the interconnection between the above components of my brace with the extension means.

DESCRIPTION OF THE PREFERRED EMBODIMENT

Figure 5:
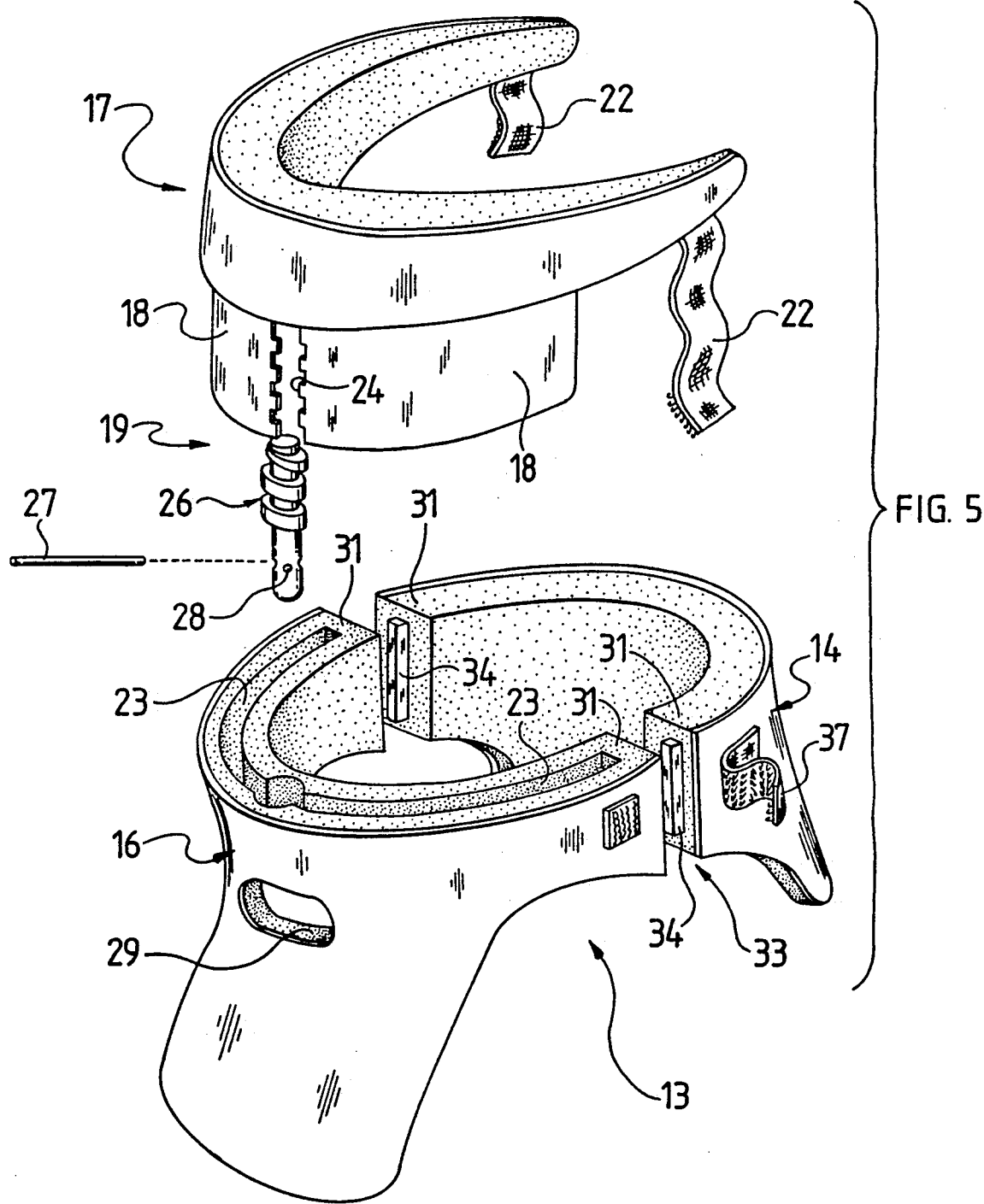
FIG. 5 is an exploded perspective view of my brace showing components which comprise my brace.

FIG. 1 depicts the orientation of my brace on a human patient. My brace is positioned beneath the skull 11 and around the neck 12 of user and for greater stability and comfort my brace as shown in FIG. 1 extends downwardly from the neck 12 to cover the sternum, clavicle and anterior shoulder area and posteriorly extends downwardly to cover the posterior shoulder and scapula. Several separate members as shown in FIG. 5 are joined to form my brace. With reference to FIG. 5, the anterior base member 14 and posterior base member 16 are joined to form the base 13. A cranial support means 17 is the member supporting the skull 11. The base 13 and the cranial support means 17 are movably engaged by a depending guide 18 affixed to the cranial support means 17. The depending guide 18 is one of the components of the extension means 19.

The extension means 19 as shown in FIGS. 4 and 5 is utilized to move the cranial support means 17 relative to the base 13 of the brace. As is clearly shown in FIG. 5, the posterior base member 16 has an upwardly opening slot 23 into which the depending guide 18 fits. The depending guide 18 as illustrated in FIG. 4, a posterior view of the extension means, has located mid-line thereon a threaded groove 24. The threaded groove 24 is designed to engage a worm screw 26 as shown in FIGS. 4 and 5. When tension is not needed, the worm screw 26 engages all of the threads of the threaded groove 24. When tension therapy is needed, the rotatable worm screw 26 of the extension means which is mounted in the posterior base member can be rotated by a detachable lever 27 which is placed into an aperture 28 located on the worm screw 26 as shown in FIG. 5 resulting in movement of the cranial support means 17 relative to the base of my brace. Access to the worm screw aperture 28 by the lever 27 is through an opening 29 located mid-line of the posterior base member 16. The opening 29 is shown in FIGS. 4 and 5. My brace, however, can be used when the only treatment needed is stabilization and immobilization by not manipulating the worm screw 26 to a position where tension would be applied on the cervical vertebrae.

The cranial support means 17 as demonstrated in FIG. 1 is positioned beneath the mandibular bone 21 and extends backwardly around the base of the skull 11 and continues in an arch around the back of the neck 12 and skull 11 to the left side of the mandibular bone forming a "U" shape as is clearly shown in FIG. 5. The cranial support means 17 has a chin support means 22 as illustrated in FIG. 1 which positions the skull 11 in the cranial support means 17 properly and also acts as an apparatus for the chin to rest upon. The chin support 22 is detachably affixed to the cranial support means 17 adjacent to the human user's chin. FIG. 5 shows the chin support 22 made of a material which can be disengaged to allow the placement of the brace and adjusted to the specific human user.

Figure 3:
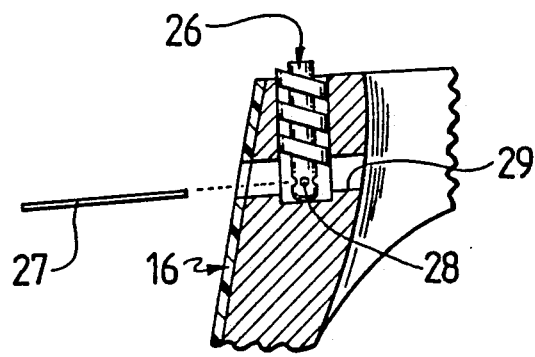
FIG. 3 is a detailed illustration of my brace's extension means along with the lever which is utilized to manipulate the extension means.
Figure 2:
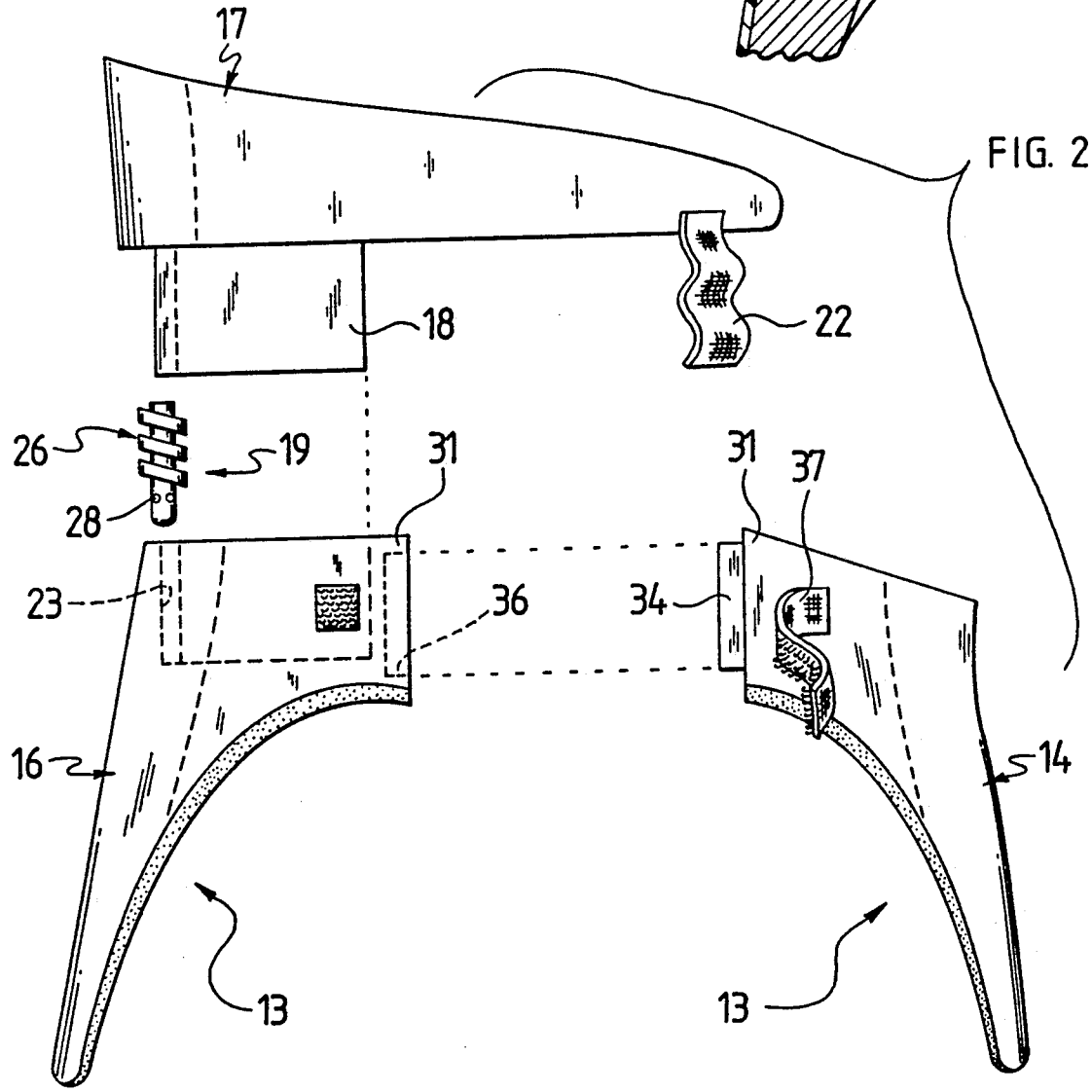
FIG. 2 is a right elevational view of my brace showing the components of said instrument separated from one another.

The base 13 of the brace is comprised of two separate components which have been joined. The base 13 as a whole is designed to emulate and contour to the neck, shoulder and posterior and anterior portions of the upper body of the human body. The anterior base member 14 as well as the posterior base member 16 having arcuate extending portions 31 which extend around the left and right sides of the neck. These arcuate extending portions 31 engage as shown in FIG. 2 to form one base unit as further illustrated in FIG. 1. FIG. 5 shows the base unit members disengaged. A connecting means 33 as shown in FIGS. 1, 2 and 5 is utilized to secure the anterior base member 14 and the posterior base member 17 into one base unit. The connecting means 33 as shown clearly in FIG. 2 is comprised of a rearwardly extending vertical plate 34 formed on the extending arcuate portion 31 of the anterior base member 14 which slides into a vertical forwardly opening slot 36 located on the posterior base member's 16 arcuate portion 31. The vertical slot 36 and the vertical plate 34 are held in this arrangement by a connecting strap 37 located adjacent to the vertical plate 34 and the vertical slot 36 and attached to the external surface of the anterior and posterior base members.

To use my brace, the posterior base member 17 is detached from the anterior base member 14 by disengaging the connecting means 33. Once the base is separated, the user's skull 11 and neck 12 are positioned within the "U" shape of the cranial support means 17 and posterior base member 16 as is shown in FIG. 5. The anterior base member 14 is repositioned and secured to the posterior base member by the connecting means 33. The skull 11 is properly positioned against the internal arch of the cranial support means 17 by the chin support means 22 which can be adjusted to compensate for different anatomical features of the user. If the patient only needs support and stabilization the extension means is not utilized. If tension is needed, the detachable lever 27 is placed into an aperture 28 of the mounted worm screw 26 and the worm screw 26 engages the grooves of the treaded groove 24 and causes the cranial support means 17 to move relative to the base. The distance between the base and the cranial support means 17 can be adjusted as greater or lesser applied tension is needed. Mobility of the user is not effected by the use of my brace for tension therapy is as much as the lightweight apparatus may be worn without additional tension creating apparatus.

While I have shown my invention in various forms, it will be obvious to those skilled in the art that it is not so limited but is susceptible of various changes and modifications without departing from the spirit thereof.

What I claim is:

1. An apparatus for supporting and stabilizing the cervical vertebrae in a human patient under various levels of extension thereof comprising:
    a. an anterior base member resting on the sternum, clavicle and anterior shoulder area with an upwardly extending arcuate portion adjacent to the anterior neck area;
    b. a posterior base member resting on the scapula and posterior shoulder area of the patient with an upwardly extending arcuate portion adjacent to the posterior neck region;
    c. connecting means securing said anterior base member to said posterior base member on both the right and left side of neck;
    d. cranial support means adapted to be positioned beneath the mandibular bone and the base of the cranial cavity for support thereof and extending about the skull from the right chin area to the left chin area;
    e. an extension means connecting said posterior base member and said cranial support means for moving said cranial support means to various positions relative to said posterior base member to selectively extend the cervical spine; and
    f. a chin support detachably affixed to the cranial support means.

2. An apparatus as defined in claim 1 wherein said extension means comprises a worm screw vertically aligned and rotatably mounted in said posterior base member said posterior base member having an opening therein cooperatively positioned to allow access to said worm screw with a detachable lever.

3. An apparatus as defined in claim 2 wherein said extension means further comprises a depending guide affixed to said cranial support means.

4. An apparatus as defined in claim 3 wherein said posterior base member has an upwardly opening slot for placement of said depending guide of the cranial support means.

5. An apparatus as defined in claim 3 wherein said extension means further comprises a threaded groove in said depending guide for engaging said worm screw.

6. An apparatus as defined in claim 1 wherein said connecting means comprises forwardly opening vertical slots located on the posterior base member on either side of the neck which are engagable with rearwardly extending vertical plates formed on the anterior base member on either side of the neck and a detachable hooked and looped strap connector mounted adjacent to said slot and plate securing said anterior and posterior base members to form a base.

7. An apparatus supporting and stabilizing the cervical vertebrae in a human patient for applying tension thereto if needed comprising:
    (a) a base comprised of an anterior base member connected to a posterior base member by a connecting means wherein said connecting means comprises forwardly opening slots located on the posterior base member on either side of the neck which are engagable with rearward extending vertical plates formed on the anterior base member on either side of neck secured together by a strap connector;
    (b) a cranial support means for supporting the skull and movable upwardly relative to said base; and
    (c) an extension means for moving said cranial support means relative to said base.

8. An apparatus as defined in claim 7 wherein said strap connector comprises a hooked and loop cloth mounted adjacent to the vertical slots and the vertical plates on the outer surface of said anterior base member and posterior base member.

9. An apparatus supporting and stabilizing the cervical vertebrae in a human patient for applying tension thereto if needed comprising:
 (a) a base;
 (b) a cranial support means for supporting the skull and movable upwardly relative to said base wherein said cranial support means extends in generally U-shape from the left side of the skull to the right side of skull positioned beneath the mandibular bone; and
 (c) an extension means for moving said cranial support means relative to said base.

10. An apparatus as defined in claim 9 wherein said cranial support means has affixed thereto a chin support comprises of a detachable cloth which extends beneath the user's chin.

11. An apparatus as supporting and stabilizing the cervical vertebrae in a human patient for applying tension thereto if needed comprising:
 (a) a base;
 (b) a cranial support means for supporting the skull and movable upwardly relative to said base; and
 (c) an extension means for moving said cranial support means relative to said base wherein said extension means comprises a depending guide mounted on said cranial support means with a threaded groove for engaging a rotatable worm screw mounted in said base for rotation by a detachable lever engagable in one or more apertures in said worm screw such that said cranial support means may be moved relative to the base.

12. An apparatus as defined in claim 11 wherein said aperture is of said worm screw accessible through an opening positioned externally, posterior and mid-line of said base.

13. An apparatus as defined in claim 1 wherein a depending guide is received into an upwardly adjacent opening slot of the posterior base member.

* * * * *